United States Patent
Means (10) Patent No.: US 8,207,185 B2
(45) Date of Patent: Jun. 26, 2012

(54) CAMKKβ AS A TARGET FOR TREATING OBESITY

(75) Inventor: Anthony R. Means, Chapel Hill, NC (US)

(73) Assignee: Duke University, Durham, NC (US)

( * ) Notice: Subject to any disclaimer, the term of this patent is extended or adjusted under 35 U.S.C. 154(b) by 463 days.

(21) Appl. No.: 12/444,260

(22) PCT Filed: Oct. 4, 2007

(86) PCT No.: PCT/US2007/021293
§ 371 (c)(1),
(2), (4) Date: Apr. 15, 2009

(87) PCT Pub. No.: WO2008/045273
PCT Pub. Date: Apr. 17, 2008

(65) Prior Publication Data
US 2010/0105716 A1    Apr. 29, 2010

Related U.S. Application Data

(60) Provisional application No. 60/829,195, filed on Oct. 12, 2006.

(51) Int. Cl.
*A61K 31/44* (2006.01)
*A61K 31/519* (2006.01)
*A61K 31/47* (2006.01)
*A61K 31/415* (2006.01)

(52) U.S. Cl. .................. 514/283; 514/265.1; 514/307; 514/394; 514/909

(58) Field of Classification Search .................. 514/283, 514/265.1, 307, 394, 909
See application file for complete search history.

(56) References Cited

U.S. PATENT DOCUMENTS

| | | | |
|---|---|---|---|
| 2,820,037 A | | 1/1958 | Schmidt-Nickels |
| 2005/0208472 A1 | | 9/2005 | Xu et al. |

FOREIGN PATENT DOCUMENTS

JP    2003-012516    1/2003

OTHER PUBLICATIONS

Tokumitsu H et al. STO-609, a specific inhibitor of the $Ca^{2+}$/calmodulin-dependent protein kinase kinase. The Journal of Biological Chemistry. May 3, 2002. 277(18): 15813-15818.

Tokumitsu H et al. A single amino acid difference between α and β $Ca^{2+}$/calmodulin-dependent protein kinase kinase dictates sensitivity to the specific inhibitor, STO-609. The Journal of Biological Chemistry. Mar. 28, 2003; 278(13): 10908-10913.

Towler MC and Hardie DG. AMP-activated protein kinase in metabolic control and insulin signaling. Circulation Research. 2007; 100: 328-341.

International Search Report and Written Opinion, PCT/US07/21293, mailed May 27, 2008.

Anderson KA et al. Hypothalamic CaMKK2 contributes to the regulation of energy balance. Cell Metabolism. May 2008; 7: 377-388.

Iughetti L et al. Pharmacological treatment of obesity in children and adolescents: present and future. Journal of Obesity. vol. 2011, Article ID 928165, 13 pages.

*Primary Examiner* — Kevin E Weddington
(74) *Attorney, Agent, or Firm* — Myers Bigel Sibley & Sajovec, P.A.

(57) ABSTRACT

A method of treating a condition in a subject in need thereof, comprising administering a calcium/calmodulin dependency kinase kinase (CaMKK) inhibitor in a treatment-effective amount. Conditions which may be treated include obesity (particularly adult obesity), insulin resistance (including high fat diet-induced insulin resistance), hyperglycemia (including hyperglycemia accompanying obesity), diabetes, etc.

7 Claims, 2 Drawing Sheets

Figure 1: Infusion of STO-609 into the Third Ventricle of Living Mice Results in Decreased Levels of NPY and AgRP mRNAs

Figure 2: Infusion of STO-609 into the Third Ventricle of Living Mice Results in Decreased Food Intake and Weight Loss within 7 Days

CAMKKβ AS A TARGET FOR TREATING OBESITY

RELATED APPLICATIONS

This application is a national phase application of PCT Application PCT/US2007/021293, filed Oct. 4, 2007, and published in English on Apr. 17, 2008, as International Publication No. WO 2008/045273, and which claims priority from and the benefit under 35 U.S.C. §119(e) of U.S. Provisional Patent Application Ser. No. 60/829,195, filed Oct. 12, 2006, the disclosure of each of which is incorporated by reference herein in its entirety.

FIELD OF THE INVENTION

The present invention concerns compounds, compositions and methods for the treatment of obesity, diabetes, insulin resistance, and hyperglycemia.

BACKGROUND OF THE INVENTION

U.S. Pat. No. 2,820,037 to Schmidt-Nickels describes compounds useful as intermediates for synthesizing dyes of the general formula:

where X is CN, COOH or COCl. The compound where X is COOH is referred to in later literature as "STO-609" (see below). Other related compounds useful in the dye industry are described in U.S. Pat. Nos. 4,336,383; 4,239,868; 3,960,867; 3,953,452; 2,949,467; 2,965,644; and 2,835,674.

Japanese Patent Application No. 2003-012516 by Sumitomo Pharmaceutical Co. describes compounds of the general formula:

wherein $R^1$ and $R^2$ are independently H, halo, alkyl, or haloalkyl, $R^3$ is H, alkyl, or substituted alkyl, or three COOR(s) may be substituted at any location on the naphthalene ring. The compounds are said to be useful in the high throughput screening of calcium/calmodulin dependency kinase kinase (CaMKK) inhibitors, in the bioactivities in which CaMKK participates, and to offer CaMKK inhibitors useful as drugs. See also H. Tokumitsu et al., *J. Biol. Chem.* 277, 15813-15818 (2002), which describes STO-609 as a specific inhibitor of the $Ca^{2+}$/calmodulin-dependent protein kinase kinase (CaMKK) and as "a useful tool for evaluating the regulatory roles of caM-KK for various physiological functions" and as a tool to "distinguish between the functions of the two CaM-KK isoforms". Id. at 15817.

SUMMARY OF THE INVENTION

A first aspect of the present invention is an active compound as described herein.

A second aspect of the present invention is a method of treating a condition in a subject in need thereof, comprising administering an active compound as described herein in a treatment-effective amount. Conditions which may be treated include obesity (particularly adult obesity), insulin resistance (including high fat diet-induced insulin resistance), hyperglycemia (including hyperglycemia accompanying obesity), etc.

A still further aspect of the present invention is a composition comprising an active agent as described herein in combination with a pharmaceutically acceptable carrier.

A still further aspect of the present invention is the use of an active agent (in some embodiments including STO-609 and analogs thereof) as described herein for the preparation of a medicament for the treatment of a disorder as described above.

DETAILED DESCRIPTION OF PREFERRED EMBODIMENTS

The term "treat" as used herein refers to any type of treatment that imparts a benefit to a patient afflicted with a disease, including improvement in the condition of the patient (e.g., in one or more symptoms), prevent the development of disease, delay the onset of the disease, etc.

"Diabetes" as used herein includes any types of diabetes, particularly type II diabetes and pre-diabetes.

The term "pharmaceutically acceptable" as used herein means that the compound or composition is suitable for administration to a subject to achieve the treatments described herein, without unduly deleterious side effects in light of the severity of the disease and necessity of the treatment.

Active compounds of the present invention may optionally be administered in conjunction with other compounds useful in the treatment of diabetes, such as insulin or other insulin mimetics. The other compounds may optionally be administered concurrently. As used herein, the word "concurrently" means sufficiently close in time to produce a combined effect (that is, concurrently may be simultaneously, or it may be two or more events occurring within a short time period before or after each other).

As used herein, the administration of two or more compounds "in combination" means that the two compounds are administered closely enough in time that the presence of one alters the biological effects of the other. The two compounds may be administered simultaneously (i.e., concurrently) or sequentially. Simultaneous administration may be carried out by mixing the compounds prior to administration, or by administering the compounds at the same point in time but at different anatomic sites or using different routes of administration.

"Halo" as used herein refers to any suitable halogen, including —F, —Cl, —Br, and —I.

"Mercapto" as used herein refers to an —SH group.

"Azido" as used herein refers to an —N$_3$ group.

"Cyano" as used herein refers to a —CN group.

"Hydroxyl" as used herein refers to an —OH group.

"Nitro" as used herein refers to an —NO$_2$ group.

"Alkyl" as used herein alone or as part of another group, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, iso-pentyl, neopentyl, n-hexyl, 3-methylhexyl, 2,2-dimethylpentyl, 2,3-dimethylpentyl, n-heptyl, n-octyl, n-nonyl, n-decyl, and the like. "Lower alkyl" as used herein, is a subset of alkyl, in some embodiments preferred, and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like. The term "alkyl" or "loweralkyl" is intended to include both substituted and unsubstituted alkyl or loweralkyl unless otherwise indicated and these groups may be substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a poly-alkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Alkenyl" as used herein alone or as part of another group, refers to a straight or branched chain hydrocarbon containing from 1 to 10 carbon atoms (or in loweralkenyl 1 to 4 carbon atoms) which include 1 to 4 double bonds in the normal chain. Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadiene, and the like. The term "alkenyl" or "loweralkenyl" is intended to include both substituted and unsubstituted alkenyl or loweralkenyl unless otherwise indicated and these groups may be substituted with groups as described in connection with alkyl and loweralkyl above.

"Alkynyl" as used herein alone or as part of another group, refers to a straight or branched chain hydrocarbon containing from 1 to 10 carbon atoms (or in loweralkynyl 1 to 4 carbon atoms) which include 1 triple bond in the normal chain. Representative examples of alkynyl include, but are not limited to, 2-propynyl, 3-butynyl, 2-butynyl, 4-pentynyl, 3-pentynyl, and the like. The term "alkynyl" or "loweralkynyl" is intended to include both substituted and unsubstituted alkynyl or loweralknynyl unless otherwise indicated and these groups may be substituted with the same groups as set forth in connection with alkyl and loweralkyl above.

"Alkoxy" as used herein alone or as part of another group, refers to an alkyl or loweralkyl group, as defined herein (and thus including substituted versions such as polyalkoxy), appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

"Acyl" as used herein alone or as part of another group refers to a —C(O)R radical, where R is any suitable substituent such as aryl, alkyl, alkenyl, alkynyl, cycloalkyl or other suitable substituent as described herein.

"Haloalkyl" as used herein alone or as part of another group, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, 2-chloro-3-fluoropentyl, and the like.

"Alkylthio" as used herein alone or as part of another group, refers to an alkyl group, as defined herein, appended to the parent molecular moiety through a thio moiety, as defined herein. Representative examples of alkylthio include, but are not limited, methylthio, ethylthio, tert-butylthio, hexylthio, and the like.

"Aryl" as used herein alone or as part of another group, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated and these groups may be substituted with the same groups as set forth in connection with alkyl and loweralkyl above.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Amino" as used herein means the radical —NH$_2$.

"Alkylamino" as used herein alone or as part of another group means the radical —NHR, where R is an alkyl group.

"Arylalkylamino" as used herein alone or as part of another group means the radical —NHR, where R is an arylalkyl group.

"Disubstituted-amino" as used herein alone or as part of another group means the radical —NR$_a$R$_b$, where R$_a$ and R$_b$ are independently selected from the groups alkyl, haloalkyl, alkenyl, alkynyl, cycloalkyl, cycloalkylalkyl, aryl, arylalkyl, heterocyclo, heterocycloalkyl.

"Acylamino" as used herein alone or as part of another group means the radical —NR$_a$R$_b$, where R$_a$ is an acyl group as defined herein and R$_b$ is selected from the groups hydrogen, alkyl, haloalkyl, alkenyl, alkynyl, cycloalkyl, cycloalkylalkyl, aryl, arylalkyl, heterocyclo, heterocycloalkyl.

"Acyloxy" as used herein alone or as part of another group means the radical —OR, where R is an acyl group as defined herein.

"Ester" as used herein alone or as part of another group refers to a —C(O)OR radical, where R is any suitable substituent such as alkyl, cycloalkyl, alkenyl, alkynyl or aryl.

"Formyl" as used herein refers to a —C(O)H group.

"Carboxylic acid" as used herein refers to a —C(O)OH group.

"Sulfoxyl" as used herein refers to a compound of the formula —S(O)R, where R is any suitable substituent such as alkyl, cycloalkyl, alkenyl, alkynyl or aryl.

"Sulfonyl" as used herein refers to a compound of the formula —S(O)(0)R, where R is any suitable substituent such as alkyl, cycloalkyl, alkenyl, alkynyl or aryl.

"Sulfonate" as used herein refers to a compound of the formula —S(O)(0)OR, where R is any suitable substituent such as alkyl, cycloalkyl, alkenyl, alkynyl or aryl.

"Sulfonic acid" as used herein refers to a compound of the formula —S(O)(O)OH.

"Amide" as used herein alone or as part of another group refers to a —C(O)NR$_a$R$_b$ radical, where R$_a$ and R$_b$ are any suitable substituent such as alkyl, cycloalkyl, alkenyl, alkynyl or aryl.

"Sulfonamide" as used herein alone or as part of another group refers to a —S(O)$_2$NR$_a$R$_b$ radical, where R$_a$ and R$_b$ are any suitable substituent such as H, alkyl, cycloalkyl, alkenyl, alkynyl or aryl.

"Urea" as used herein alone or as part of another group refers to an —N(R$_c$)C(O)NR$_a$R$_b$ radical, where R$_a$, R$_b$ and R$_c$ are any suitable substituent such as H, alkyl, cycloalkyl, alkenyl, alkynyl or aryl.

"Alkoxyacylamino" as used herein alone or as part of another group refers to an —N(R$_a$)C(O)OR$_b$ radical, where R$_a$, R$_b$ are any suitable substituent such as H, alkyl, cycloalkyl, alkenyl, alkynyl or aryl.

"Aminoacyloxy" as used herein alone or as part of another group refers to an —OC(O)NR$_a$R$_b$ radical, where R$_a$ and R$_b$ are any suitable substituent such as H, alkyl, cycloalkyl, alkenyl, alkynyl or aryl.

"Cycloalkyl" as used herein alone or as part of another group, refers to a saturated or partially unsaturated cyclic hydrocarbon group containing from 3, 4 or 5 to 6, 7 or 8 carbons (which carbons may be replaced in a heterocyclic group as discussed below). Representative examples of cycloalkyl include, cyclopropyl, cyclobutyl, cyclopentyl, cyclohexyl, cycloheptyl, and cyclooctyl. These rings may be optionally substituted with additional substituents as described herein such as halo or loweralkyl. The term "cycloalkyl" is generic and intended to include heterocyclic groups as discussed below unless specified otherwise.

"Heterocyclic group" or "heterocyclo" as used herein alone or as part of another group, refers to an aliphatic (e.g., fully or partially saturated heterocyclo) or aromatic (e.g., heteroaryl) monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, aryl alkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

The present invention is primarily concerned with the treatment of human subjects, but the invention may also be carried out on animal subjects, particularly mammalian subjects such as mice, rats, dogs, cats, livestock and horses for veterinary purposes, and for drug screening and drug development purposes. The subjects may be of any age, with adolescent, adult, and geriatric subjects particularly preferred.

1. Active Compounds.

Active compounds useful for carrying out the present invention include calcium/calmodulin dependency kinase kinase (CaMKK) inhibitors (particularly CaMKKβ inhibitors).

Active compounds useful for carrying out the present invention include ATP-mimics.

Active compounds useful for carrying out the present invention include benzimidazoisoquinolines such as STO-609 and analogs thereof (see, e.g., Formula I below).

Active compounds for carrying out the present invention include compounds of Formula I:

(I)

wherein:

R$^1$, R$^2$, R$^3$, R$^4$, R$^5$, R$^6$, R$^7$, R$^{7a}$, R$^8$, R$^9$, R$^{10}$, and R$^{11}$ are each independently selected from the group consisting of: H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, and aminoacyloxy;

or a pharmaceutically acceptable salt or prodrug thereof.

In some embodiments, R$^7$ and R$^{7a}$ preferably together form oxo (=O).

In some embodiments, R$^7$ and R$^{7a}$ preferably do not form oxo (=O).

In some embodiments, $R^3$ is preferably —COOH, —CH$_2$COOH, —CH$_2$CH$_2$COOH, or an ester thereof.

In some embodiments, $R^1$, $R^2$, $R^4$, $R^5$, $R^6$, $R^7$, $R^8$, $R^9$, $R^{10}$, $R^{11}$ are all H.

In some embodiments, at least one, two, or three of $R^1$, $R^2$, $R^4$, $R^5$, $R^6$, $R^7$, $R^8$, $R^9$, $R^{10}$, and $R^{11}$ is not H. Thus, in some embodiments, $R^1$ is not H; in some embodiments $R^2$ is not H; in some embodiments $R^3$ is not H; in some embodiments $R^4$ is not H; in some embodiments $R^5$ is not H; in some embodiments $R^6$ is not H; in some embodiments $R^7$ is not H; in some embodiments $R^9$ is not H; in some embodiments $R^{10}$ is not H; and/or in some embodiments $R^{11}$ is not H.

Active compounds may be provided as pharmaceutically acceptable prodrugs, which are those prodrugs of the active compounds of the present invention which are, within the scope of sound medical judgment, suitable for use in contact with the tissues of humans and lower animals without undue toxicity, irritation, allergic response and the like, commensurate with a reasonable risk/benefit ratio, and effective for their intended use, as well as the zwitterionic forms, where possible, of the compounds of the invention. The term "prodrug" refers to compounds that are rapidly transformed in vivo to yield the parent compound of the above formulae, for example, by hydrolysis in blood. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299 Examples include a prodrug that is metabolized in vivo by a subject to an active drug having an activity of active compounds as described herein, wherein the prodrug is an ester of an alcohol or carboxylic acid group, if such a group is present in the compound; an acetal or ketal of an alcohol group, if such a group is present in the compound; an N-Mannich base or an imine of an amine group, if such a group is present in the compound; or a Schiff base, oxime, acetal, enol ester, oxazolidine, or thiazolidine of a carbonyl group, if such a group is present in the compound, such as described in U.S. Pat. No. 6,680,324 and U.S. Pat. No. 6,680, 322.

The active compounds disclosed herein can, as noted above, be provided in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

Active compounds as described herein can be prepared in accordance with known procedures, or variations thereof that will be apparent to those skilled in the art. See, e.g., U.S. Pat. Nos. 4,336,383; 4,239,868; 3,960,867; 3,953,452; 2,949,467; 2,965,644; 2,835,674; and 2,820,037, the disclosures of which are to be incorporated by reference herein in their entirety.

2. Pharmaceutical Formulations.

The active compounds described above may be formulated for administration in a pharmaceutical carrier in accordance with known techniques. See, e.g., Remington, *The Science And Practice of Pharmacy* (9$^{th}$ Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces), transdermal administration, and intraventricular injection (injection into a ventricle of the brain, e.g., by an implanted catheter or omman reservoir, such as in the case of morbid obesity) and although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/ dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising a compound of Formula (I), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to active compounds of formula (I) or their salts, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

3. Dosage and Routes of Administration.

As noted above, the present invention provides pharmaceutical formulations comprising the active compounds (including the pharmaceutically acceptable salts thereof), in pharmaceutically acceptable carriers for oral, rectal, topical, buccal, parenteral, intramuscular, intradermal, or intravenous, and transdermal administration.

The therapeutically effective dosage of any specific compound, the use of which is in the scope of present invention, will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the active compound, including the cases where a salt is employed. Toxicity concerns at the higher level may restrict intravenous dosages to a lower level such as up to about 10 mg/kg, with all weights being calculated based upon the weight of the active base, including the cases where a salt is employed. A dosage from about 10 mg/kg to about 50 mg/kg may be employed for oral administration. Typically, a dosage from about 0.5 mg/kg to 5 mg/kg may be employed for intramuscular injection. Preferred dosages are 1 µmol/kg to 50 µmol/kg, and more preferably 22 µmol/kg and 33 µmol/kg of the compound for intravenous or oral administration. The duration of the treatment is usually once per day for a period of two to three weeks or until the condition is essentially controlled. Lower doses given less frequently can be used prophylactically to prevent or reduce the incidence of recurrence of the infection.

The present invention is explained in greater detail in the following non-limiting Examples.

EXPERIMENTAL

We have been investigating whether CaMKKβ null mice had phenotypes consistent with a physiological role as an AMPK kinase. AMPK had been shown to function in a pathway in NYP neurons of the arcuate nucleus of the hypothalamus to regulated NPY mRNA and feeding behavior. First, we used in situ hybridization to demonstrate that CaMKKβ was expressed in the ARC whereas the other described AMPK kinase, LKB1 was not. We then demonstrated that the mRNAs encoding the NPY and AgRP neuropeptides were decreased in the hypothalamus of CaMKKβ null mice relative to WT mice. As these mRNAs are exclusively expressed in NPY neurons of the ARC, these results showed a role for CaMKKβ in these neurons. Next we showed in hypothalamic extracts that the absence of CaMKKβ resulted in decreased phosphorylation of AMPK on $T^{172}$ and AMPK protein kinase activity.

Mice were then place on normal or high fat food and body weight was monitored over a 12 week period. We were surprised to find no difference in weight between WT and CaMKKβ null mice whether fed or normal of high fat chow for 12 weeks. However, after feeding the high fat diet for an additional 12 week period, the CaMKKβ null mice weighed significantly less than the WT mice (data not shown). Evaluation of food intake showed that the CaMKKβ mice eat about 30% less than WT mice whether fed on a high fat diet (data not shown). To evaluate the potential mechanism for why decreased food intake did not correlate with decreased body weight, mice were subjected to analysis in metabolic chambers. Even on the normal diet, CaMKKβ mice consumed 30% less $O_2$, produced 30% less $CO_2$ and heat. However, the respiratory quotient did not change showing that there was no difference in the type of food used to supply energy and the WT and CaMKKβ mice showed a similar degree of activity. Together these data suggested that the absence of CaMKKβ resulted in decreased food intake together with more efficient caloric utilization.

Because the mice eat less and enjoyed more efficient metabolism when fed a high fat diet we subjected them to a glucose tolerance test (data not shown). Both WT and CaMKKβ mice performed similarly when fed on the normal lab chow. However, when fed the high fat diet, the CaMKKβ null mice remained glucose tolerant whereas the WT mice showed glucose intolerance and hyperglycemia. An insulin tolerance test was next administered (data not shown). Again, both WT and CaMKKβ null mice were insulin tolerant when fed the normal diet. However, whereas the WT mice demonstrated insulin resistance when fed the high fat diet, the CaMKKβ null mice continued to show insulin tolerance.

Several hormones are known to be involved in feeding behavior and energy balance. We measure three of these hormones in the serum of WT and CaMKKβ mice fed on normal diet (data not shown). Whereas Adiponectin and Ghrelin levels were unchanged between the two strains of mice, Leptin levels were increased two-fold in the CaMKKβ null mice and this difference from WT was highly statistically significant. Increased Leptin is entirely consistent with decreased food intake and more efficient energy balance in mice lacking CaMKKβ (data not shown).

If NPY is regulating feeding behavior, why do the CaMKKβ mice maintain weight on normal lab chow? The potential reason can be gleaned from the NPY literature. In 1984 NPY was administered directly into the brain of rats. This was shown to acutely increase feeding and chronically lead to diabetes. The first knock-out of the NPY gene was described in 1996. The mice analyzed were of a mixed genetic background (129/C57BL6) and showed no alterations in feeding or energy balance, which was in apparent contradiction to the 1984 study. Then, in 2003, the NPY gene deletion was studied in an isogenic C57BL6/J genetic background. In this case there was an increase in body weight and decreased re-feeding response after a fast. Most recently, in late 2005, the effect of ablation of NPY neurons was reported. When this was done in neonates, there was no effect on feeding. However, when done in adult mice, rapid starvation ensued. Based on this collective information it seems certain that compensatory mechanisms develop after depletion of NPY in neonates to maintain energy balance. Since in our study of the effects of CaMKKβ gene deletion, animals were without the gene throughout development, it seemed logical to presume that compensatory mechanism occurred to moderate the effects of loss of the gene. To test this idea it was necessary to examine the effects of acute down-regulation of CaMKKβ in adult WT mice.

Figure 1:
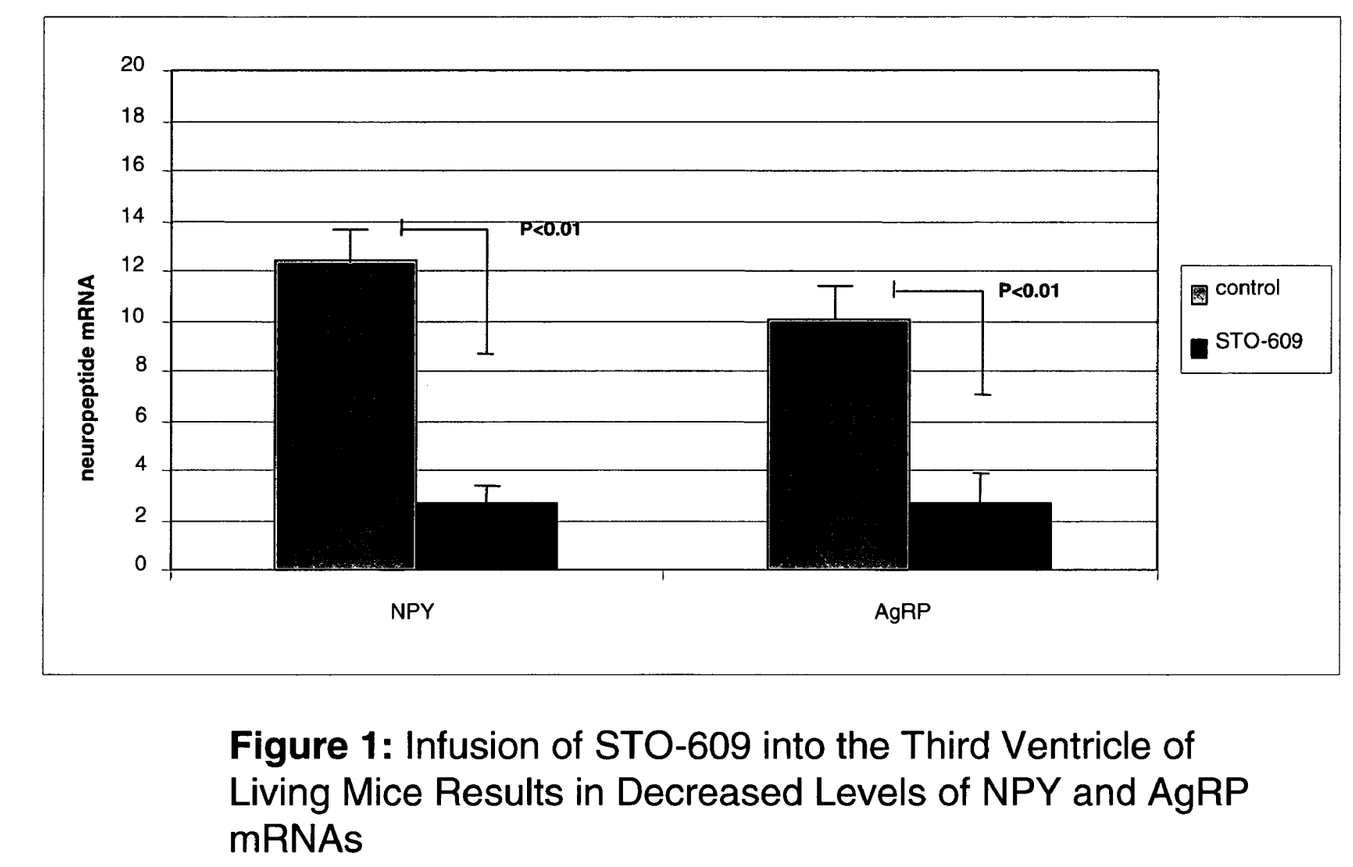
FIG. 1: Infusion of STO-609 into the Third Ventricle of Living Mice Results in Decreased Levels of NPY and AgRP mRNAs.
Figure 2:
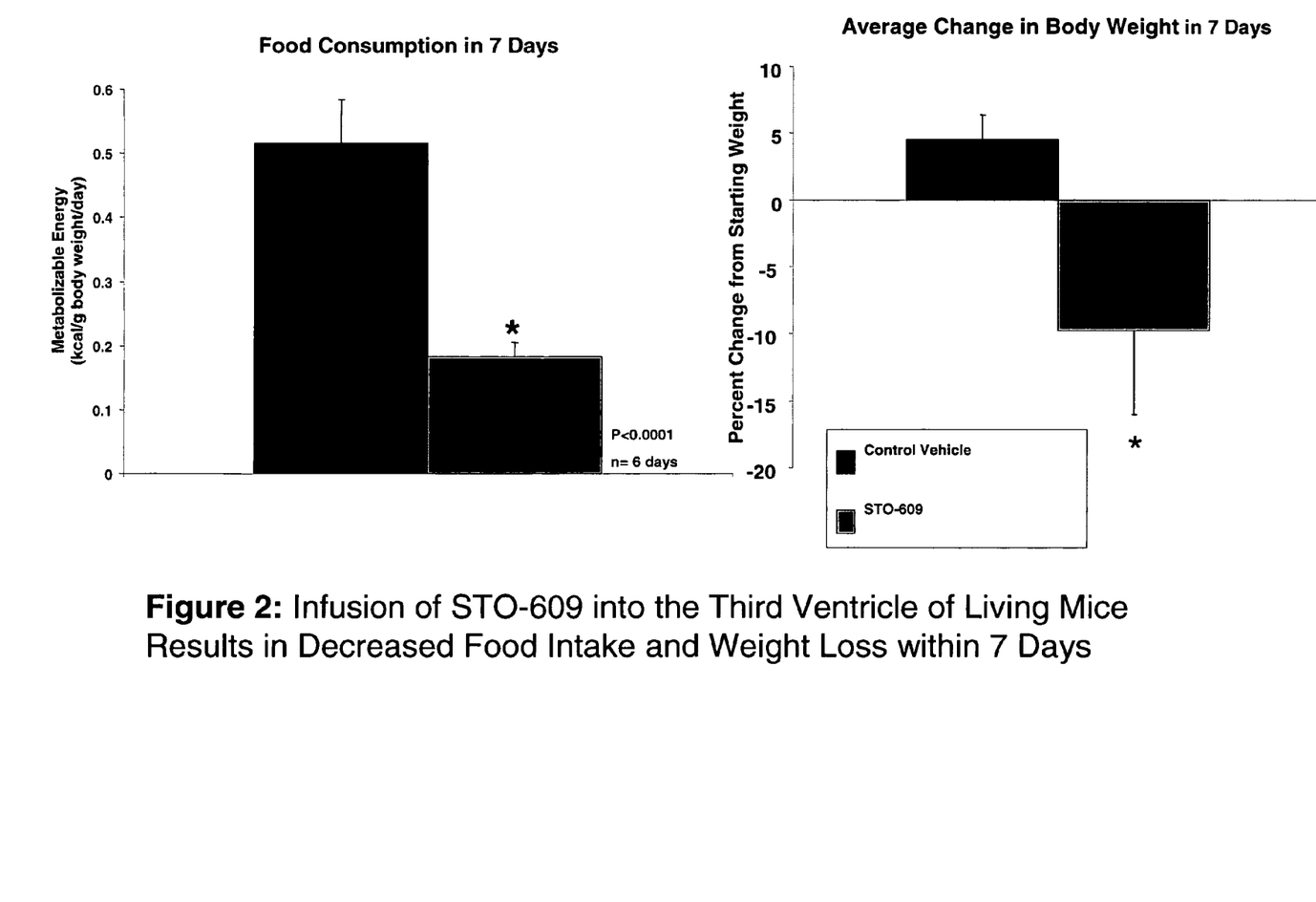
FIG. 2: Infusion of STO-609 into the Third Ventricle of Living Mice Results in Decreased Food Intake and Weight Loss within 7 Days

STO-609 is a small molecule inhibitor of CaMKKβ (it also inhibits CaMKKα). Whereas this inhibitor is highly selective for the CaMKKs in vitro, it will inhibit other protein kinases at higher concentrations. To test the effect of STO-609 on feeding behavior, we stereotaxically implanted cannula into the third ventricle of living mice and attached the cannula to osmotic min-pumps that distribute fluids at a rate of 0.5 ul/hr for 7 days. Half of the pumps contained 20 uM STO-609 whereas the other half contained the NaOH vehicle. We monitored body weight together with food and water intake daily for 7 days. Then the mice were sacrificed, hypothalami were removed, RNA extracted and the mRNAs encoding NPY and AgRP were quantified by RT-PCR. We found highly statistically significant decreases in NPY and AgRP mRNA in the hypothalamic RNA isolated from mice that had been dosed with STO-609 (FIG. 1). This showed that the drug had effects specifically on the NPY neurons. In addition, STO-609 decreased the total amount of food consumed over the 7 day period by 60% (FIG. 2, left panel) but had no effect on water consumption. In addition, whereas the WT mice gained body weight during the 7 day period (about 4% relative to the starting weight) the STO-609 treated mice lost weight (about 7% relative to the starting weight) (FIG. 2, right panel).

These data show that an inhibitor of CaMKKβ can acutely decrease food intake and lead to weight loss when administered into the third ventricle of mice.

The foregoing is illustrative of the present invention, and is not to be construed as limiting thereof. The invention is defined by the following claims, with equivalents of the claims to be included therein.

What is claimed is:
1. A method of treating obesity in a subject in need thereof, comprising administering said subject a calcium/calmodulin dependency kinase kinase (CaMKK) inhibitor in a treatment-effective amount, wherein said CaMKK inhibitor is a compound of Formula I:

(I)

wherein:
$R^1$, $R^2$, $R^3$, $R^4$, $R^5$, $R^6$, $R^7$, $R^{7a}$, $R^8$, $R^9$, $R^{10}$, and $R^{11}$ are each independently selected from the group consisting of: H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, hetero aryl alkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, and aminoacyloxy;

or a pharmaceutically acceptable salt thereof.

2. The method of claim 1, wherein $R^7$ and $R^{7a}$ together form oxo (=O).

3. The method of claim 1, wherein $R^7$ and $R^{7a}$ do not form oxo (=O).

4. The method of claim 1, wherein $R^3$ is selected from the group consisting of —COOH, —CH$_2$COOH, —CH$_2$CH$_2$COOH, or an ester thereof.

5. The method of claim 1, wherein $R^1$, $R^2$, $R^4$, $R^5$, $R^6$, $R^7$, $R^8$, $R^9$, $R^{10}$, and $R^{11}$ are all H.

6. The method of claim 1, wherein at least one of $R^1$, $R^2$, $R^4$, $R^5$, $R^6$, $R^7$, $R^8$, $R^9$, $R^{10}$, and $R^{11}$ is not H.

7. The method of claim 1, wherein:
$R^7$ and $R^{7a}$ together form oxo (=O);
$R^3$ is selected from the group consisting of —COOH, —CH$_2$COOH, and —CH$_2$CH$_2$COOH; and
$R^1$, $R^2$, $R^4$, $R^5$, $R^6$, $R^7$, $R^8$, $R^9$, $R^{10}$, and $R^{11}$ are all H.

* * * * *

UNITED STATES PATENT AND TRADEMARK OFFICE
CERTIFICATE OF CORRECTION

| | | |
|---|---|---|
| PATENT NO. | : 8,207,185 B2 | Page 1 of 1 |
| APPLICATION NO. | : 12/444260 | |
| DATED | : June 26, 2012 | |
| INVENTOR(S) | : Means | |

It is certified that error appears in the above-identified patent and that said Letters Patent is hereby corrected as shown below:

Column 12, Claim 1, Line 64: Please correct "hetero aryl alkyl,"
to read -- heteroarylalkyl --

Signed and Sealed this
Eighteenth Day of December, 2012

David J. Kappos
*Director of the United States Patent and Trademark Office*